United States Patent [19]

Julian et al.

[11] Patent Number: 4,851,226

[45] Date of Patent: Jul. 25, 1989

[54] CHEWABLE MEDICAMENT TABLET CONTAINING MEANS FOR TASTE MASKING

[75] Inventors: Thomas N. Julian, Horsham; Galen W. Radebaugh, Maple Glen, both of Pa.

[73] Assignee: McNeil Consumer Products Company, Fort Washington, Pa.

[21] Appl. No.: 214,265

[22] Filed: Jun. 30, 1988

Related U.S. Application Data

[63] Continuation-in-part of Ser. No. 121,692, Nov. 16, 1987, abandoned.

[51] Int. Cl.$^4$ .................................................. A61K 9/32
[52] U.S. Cl. ..................................... 424/441; 424/472; 424/480; 424/482; 424/470; 424/481; 424/3
[58] Field of Search ............... 424/441, 470, 472, 480, 424/482, 494, 497

[56] References Cited

U.S. PATENT DOCUMENTS

| | | | |
|---|---|---|---|
| 2,954,322 | 9/1960 | Heilig et al. | 424/481 |
| 3,133,863 | 5/1964 | Tansey | 424/465 |
| 3,371,015 | 2/1968 | Sjogren et al. | 424/482 |
| 3,420,931 | 1/1969 | Daum et al. | 424/33 |
| 3,458,622 | 7/1969 | Hill | 424/468 |
| 3,741,795 | 6/1973 | Signorino | 117/100 |
| 3,847,822 | 11/1974 | Shuey et al. | 210/528 |
| 3,950,508 | 4/1976 | Mony et al. | 424/19 |
| 4,079,125 | 3/1978 | Sipos | 424/484 |
| 4,244,789 | 1/1981 | Coll-Palagos | 204/20 |
| 4,252,786 | 2/1981 | Weiss et al. | 424/495 |
| 4,415,547 | 11/1983 | Yu et al. | 424/469 |

FOREIGN PATENT DOCUMENTS

| | | |
|---|---|---|
| 900824 | 2/1985 | Belgium . |
| 212641 A2 | 3/1987 | . |
| 85/9645 | 12/1985 | South Africa . |
| 2025227 | 1/1980 | United Kingdom . |

Primary Examiner—Thurman K. Page
Assistant Examiner—L. Horne
Attorney, Agent, or Firm—Charles J. Metz

[57] ABSTRACT

Chewable medicament tablets are made from coated granules of medicament wherein the coating on said granules comprises a blend of cellulose acetate or cellulose acetate butyrate and polyvinyl pyrrolidone.

8 Claims, 2 Drawing Sheets

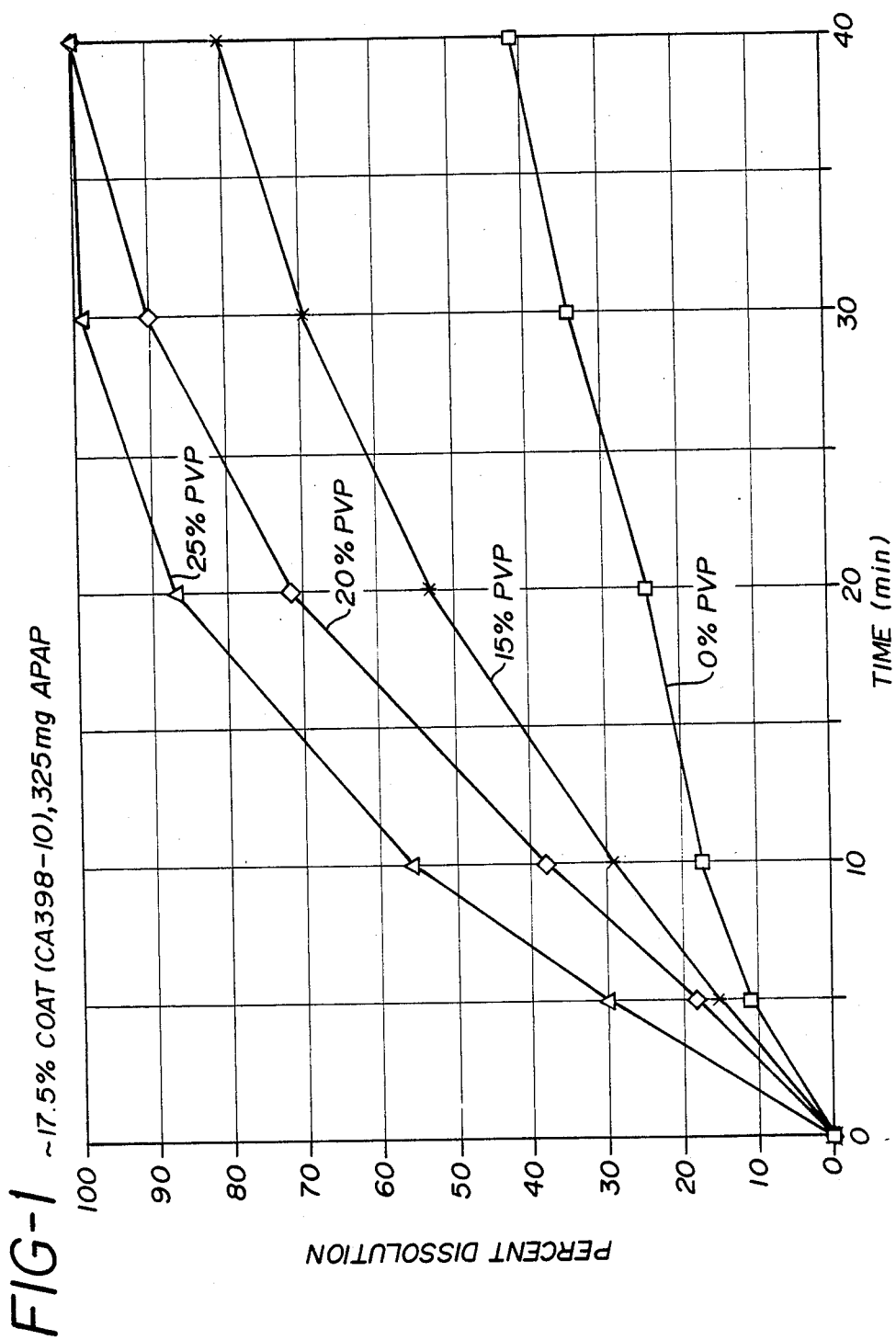

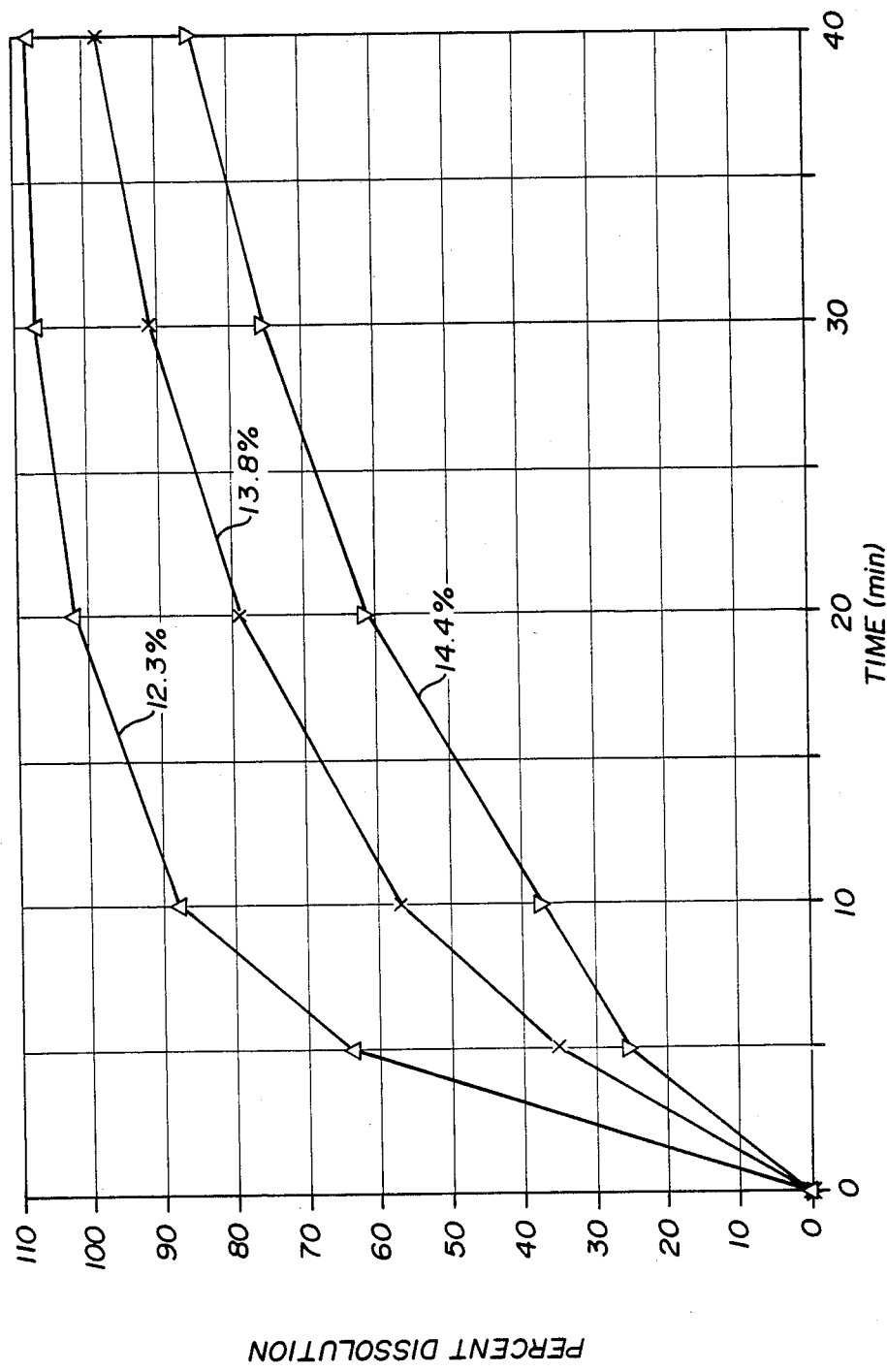

CHEWABLE MEDICAMENT TABLET CONTAINING MEANS FOR TASTE MASKING

This application is a continuation-in-part of our co-pending application Ser. No. 121,692, filed on Nov. 16, 1987, now abandoned.

The invention relates to chewable tablets containing means to mask the taste of the active ingredient.

BACKGROUND OF THE INVENTION

Orally administered medicaments are given to the patient in many forms, such as liquid solutions, emulsions, or suspensions, or in solid form such as capsules or tablets (as used herein, the term "tablet" means any shaped and compressed solid dosage form, including caplets). Medicaments administered in tablet or capsule form are usually intended to be swallowed whole. Therefore, the often disagreeable taste of the active ingredient need not be taken into account in formulating the medicine, except for the provision of means to prevent the taste from being apparent during the short time that the medicine is in the mouth. Such means may include the provision of an appropriate coating on the tablet, the use of the capsule form (the gelatin outer shell of the capsule keeps the active ingredient inside until the capsule has been swallowed), or simply compressing a tablet firmly so that it will not begin to disintegrate during the short time that it is intended to be in the mouth.

Children, older persons, and many other persons have trouble swallowing whole tablets and even capsules. Therefore, in cases where the dosage to be administered cannot be made into a very small tablet or capsule, it is desirable to provide the medicine either in liquid form or in a chewable solid form, in addition to the tablet or capsule that is designed to be swallowed whole. Even where the medicine can be formulated as a liquid, it is desirable also to be able to provide a chewable solid form because it is usually more convenient to carry a supply of tablets with oneself all day than a container of liquid medicine.

In some cases, the taste of the active medicament in a tablet can be overpowered by adding flavoring ingredients to the tablet so that when it is chewed the taste of the active ingredient is simply overpowered. For instance, this has been done with children's aspirin where the dosage is small enough so that the amount of flavoring agents needed to mask the tast of the medicine is not so great that the tablet becomes unreasonably large. A children's size tablet of acetaminophen (acetyl para-aminophenol or "APAP") is available commercially wherein the APAP is present in granules that are coated with ethyl cellulose. A significant proportion of the APAP remains shielded by the coating (and therefore does not contribute to taste) while the tablet is in the mouth, despite some breakage of the ethyl cellulose coating during compression of the tablet and some additional breakage of the coating during chewing. The APAP becomes bioavailable via permeation through the coating (although ethyl cellulose is not soluble in aqueous fluids, water does permeate through the coating) and from the granules wherein the coating was broken. This invention is directed to the discovery of a coating that can be used to coat granules of active medicament and which can achieve a better balance between taste masking and control of bioavailability than can be achieved with ethyl cellulose.

BRIEF SUMMARY OF THE INVENTION

The invention provides a chewable tablet of a medicament comprising compressed particles of the medicament wherein the individual particles are coated with a blend of cellulose acetate or cellulose acetate butyrate and polyvinyl pyrrolidone (USP Povidone or "PVP"). The coating provides excellent taste masking while still permitting acceptable bioavailability of the active ingredient. In a preferred embodiment, acetaminophen particles are coated with a blend of cellulose acetate and polyvinyl pyrrolidone, and are then compressed into tablet form together with flavoring agents and other ingredients that are customarily used in making such tablets.

THE PRIOR ART

Children's chewable APAP tablets are available commercially wherein the APAP is present in granules coated with ethyl cellulose.

Heilig et al., in U.S. Pat. No. 2,954,322, disclose a tablet intended for oral administration wherein the whole tablet is coated with a mixture of shellac and polyvinyl pyrrolidone ("PVP"). It is intended that the tablet be swallowed whole and that the coating will disintegrate in the stomach to release the active medicament. A similar disclosure of a medicinal tablet coating of a mixture of shellac and PVP is found in Signorino, U.S. Pat. No. 3,741,795.

Hill, in U.S. Pat. No. 3,458,622, discloses a controlled release tablet wherein the active medicament is contained in a core comprising a matrix of a mixture of PVP and a carboxyvinyl(polyacrylic acid)hydrophilic polymer.

Weiss et al., in U.S. Pat. No. 4,252,786, disclose a controlled release tablet similar to that of Hill, wherein the core containing the active medicament is coated with a relatively insoluble, water permeable, rupturable film comprising a combination of hydrophobic and hydrophilic polymers. Cellulose acetate is disclosed as one of the hydrophobic polymers. The tablets of Weiss et al. and Hill are intended to be swallowed whole.

Yu et al., in U.S. Pat. No. 4,415,547, disclose sustained release pharmaceutical tablets consisting essentially of drug pellets encapsulated with a water-soluble film-forming substance and a water-insoluble film-forming substance and blended and compressed into tablet form with a compressible tableting mixture. In an example, sugar-starch beads are coated with theophylline and PVP to form pellets, these pellets are encapsulated in a mixture of PVP and ethyl cellulose to form encapsulated pellets, which are then compressed into tablet form with a tableting mixture. Mony et al., in U.S. Pat. No. 3,950,508, disclose another sustained-release medicinal tablet in which the active ingredient is contained in a matrix of ethyl cellulose which can contain PVP.

Boehringer Ingelheim British Pat. No. 2,025,227, published Jan. 23, 1980, discloses a pharmaceutical preparation in retard form comprising a core containing an active substance together with a carrier or excipient, said core being coated with a semipermeable coating comprising ethyl cellulose and polyethylene glycol. The core may be in the form of a tablet which is then spray coated with the coating.

Sipos, in U.S. Pat. No. 4,079,125, discloses enteric coated enzyme preparations which utilize binders, among which are PVP, microcrystalline cellulose, ethyl cellulose, cellulose acetate phthalate, and alginic acid.

The preparations are designed to be swallowed whole, to pass through the stomach unchanged, and to release the active ingredients in the intestine.

Tansey, in U.S. Pat. No. 3,133,863, discloses a method for forming granules of medicament that can then be compressed into tablet form, wherein the granules include various polymers dispersed throughout the granules. One embodiment comprises acetaminophen mixed with PVP and methyl cellulose.

Mixtures of PVP and cellulose acetate have been disclosed in utilities other than in making medicinal pills or tablets. For instance, Shuey et al., in U.S. Pat. No. 3,847,822, disclose hemodialysis membranes fabricated from PVP and cellulose acetate. Coll-Palagos, in U.S. Pat. No. 4,244,789, discloses a primer coating useful in metallization which contains PVP, cellulose acetate butyrate, and vinyl acetate-vinyl chloride copolymer.

Benedikt, in South African Patent Application No. 85/9645, discloses sustained release theophylline preparations in which the medicament was contained in a matrix of a mixture of PVP and ethyl cellulose or other water insoluble polymers such as cellulose esters, with the matrix then being coated with a coating which contains cellulose acetate butyrate. In the prior art section of this patent there are disclosed several theophylline dosage forms that provide time release of the active ingredient, including (a) a depot medicament form (apparently intended for implantation in the body) wherein theophylline is contained in spheroid medicament particles that are coated with a dialysis membrane, the film-forming agent of which consists of an insoluble cellulose ether and a soluble organic compound containing carboxyl groups, and (b) theophylline pellets coated with a lacquer of ethyl cellulose and polyethylene glycol.

Daum et al., in U.S. Pat. No. 3,420,931, sugar-coated pharmaceutical preparations ("dragees") coated with a mixture of sugar and a vinyl polymer such as PVP. The coating may also contain cellulose derivatives. Specifically disclosed cellulose derivatives are methyl cellulose, ethyl cellulose, carboxymethyl cellulose, hydroxyethyl cellulose, and hydroxypropyl cellulose.

Sjogren et al., in U.S. Pat. No. 3,371,015, disclose a medicament tablet having a two-layer coating, the inner layer being a relatively thick layer of polyethylene glycol and the outer layer being a thin layer of a water-insoluble polymer, including cellulose acetate.

Damani et al., in EPO application No. 212641 A2, published on Mar. 4, 1987 (this publication may not be prior art to applicants), disclose a chewable medicinal tablet wherein the active ingredient (which can be acetaminophen) is embedded in a matrix of polyvinyl acetate phthalate for taste masking.

In Belgian Pat. No. 900,824, issued to Elan Corp., a controlled-release medicinal tablet is disclosed. The active ingredient is contained in a core, which may contain PVP, and the core is contained within a membrane, which may consist of a mixture of cellulose acetate, polyvinyl chloride, and polyvinyl alcohol. A sugar coating is then applied to the surface of the tablet.

BRIEF DESCRIPTION OF THE DRAWINGS

FIG. 1 is a graph of percent dissolution versus time for chewable APAP tablets made in accordance with the invention, wherein the coatings on the coated granules have varying proportions of cellulose acetate to polyvinyl pyrrolidone, with the proportion of coating to medicament in the coated granules being held constant; and FIG. 2 is a graph of percent dissolution versus time for chewable APAP tablets made in accordance with the invention, wherein the coated granules have varying proportions of coating to APAP, with the polymer blend composition remaining constant.

DETAILED DESCRIPTION OF THE INVENTION

The invention will be described more specifically in terms of its preferred embodiment which is the preparation of chewable tablets of acetyl p-aminophenol (acetaminophen or "APAP"), a medicament used in both over-the-counter preparations and in prescription drugs for analgesic and antipyretic purposes. In the preferred embodiment of the process of the invention, APAP, in granular form, is coated with a blend of cellulose acetate and PVP so that the granules are coated with the polymer blend, and the thus coated granules, together with other ingredients such as flavoring agents, extenders, excipients, and the like, are compressed into tablet form. (As used herein, the term "granule" refers to individual particles or to agglomerates of individual particles of the medicament.) A high enough proportion of the coating remains effectively intact on the APAP granules through the compression of the tablet and through normal chewing in the mouth to permit effective taste masking of the APAP. (By the term "effectively intact" is meant that the coating remains sufficiently integral so as to limit the amount of the flavor of the medicament that can be detected through the coating so that the quantity of other flavoring agents that need to be used in the tablet to mask the unpleasant flavor of the medicament is not so large that an excessively large tablet is required.) However, when the granules are swallowed, the active medicament becomes bioavailable via permeation through the coating (permeation can occur through the intact coating as well as through the coating that has become porous through dissolution of the water-soluble PVP component of the coating) and via disintegration of the coating, which is caused in part by chewing, in part by processing of the tablet (compression), and in part by removal of the PVP component of the coating by dissolution. The coating may be designed so that the medicine is released relatively rapidly or in a sustained release mode, depending on the proportion of coating to medicament in the granules, on the proportion of the cellulose acetate and PVP in the coating, or a combination of the two.

The coating used is preferably a blend containing about 80 to 97 percent of cellulose acetate ("CA") (USP cellulose acetate NF is preferred), by weight of the coating, the remainder being PVP. Within the range indicated, if sustained release of the medicament is desired, a lower proportion of the PVP may be used. When rapid release of the medicament is desired, the proportion of PVP will usually be from about 12 to 20 percent. Routine experimentation will suffice to determine the appropriate proportions of the two polymers to use in individual cases, as is more specifically illustrated below. Cellulose acetate butyrate ("CAB") may be used in combination with or as a substitute for CA.

The coated granules may be made by coating the granules of medicament with an organic solvent solution of the two polymers in a fluidized bed coating operation. A wide variety of organic solvents may be used to prepare the organic solvent solution of the coating polymers. For instance, a preferred solvent is acetone-methanol, but other solvent systems may also be used, including methylene chloride ("CH$_2$Cl$_2$"), methylene chloride-methanol, acetone-ethyl acetate, acetone-ethanol, acetone, ethyl acetate, methyl ethyl ketone, and others. As a general rule, the proportion of polymer in the solvent solution will be from about 5 to 20 weight percent, depending upon the specific solvents used and other similar considerations.

The polymers are dissolved in the solvent and the polymer solution is then coated onto the APAP granules, using a fluidized bed coater. Air (which may be heated) passes through a bed of the medicament granules to fluidize them, and the solvent solution of the two polymers is sprayed onto the fluidized bed and thereby coats the granules. The air passing through the bed dries the coated granules, so that a dry coated granule is obtained. The coated granules are then used in combination with various excipients, flavors, and colors to make a chewable tablet.

The dried coating as thus applied usually constitutes about 5–20% of the total dry weight of the coated APAP granule. The exact proportions of coating to medicament desired for individual cases can be determined by routine experimentation. A larger proportion of coating may be used to provide a sustained release formulation or a better taste.

The exact size of the coated granules has not been found to be narrowly critical. For example, the coated granules will usually be sized between about 10 and 200 mesh (U.S. Sieve Series). In the usual case, the coated granules will be sized from about 40 to 60 mesh.

Cellulose acetate, and its alternative, cellulose acetate butyrate, are quite water insoluble but organic solvent soluble polymers. They can provide good taste masking properties since they won't dissolve in the mouth and are tough enough to remain effectively intact during processing and normal chewing in the mouth. But, if used alone, a coating of CA or CAB would not provide adequate bioavailability of the active ingredient after swallowing the chewed tablet. To provide the requisite bioavailability, PVP is added. It is a polymer which is soluble in both water and organic solvents. The water solubility of PVP provides the bioavailability of the active medicament in the GI tract via the mechanisms discussed above. The fact that PVP is compatible with CA and CAB in the solid state contributes to the provision of bioavailability, and probably contributes to the ability of the coating to remain effectively intact through processing of the tablet and normal chewing because the addition of PVP to the CA or CAB does not embrittle the polymer mixture as would most likely be the case if PVP were not compatible with CA or CAB. The solubility of PVP in organic solvents permits PVP to be readily mixed with CA or CAB during the production of the coated granules, since CA and CAB are not very soluble, if at all, in water, and are most conveniently applied from an organic solvent solution. The blend of CA and PVP used provides the balance needed for good taste masking while being chewed in the mouth, along with bioavailability of the active medicament in an appropriate manner (i.e., either relatively rapidly or by sustained release) in the GI tract after swallowing.

In addition to APAP, any solid medication in need of taste masking can be used in the invention. Illustrations include aspirin, ibuprofen, and loperimide.

PREPARATION OF COATED GRANULES

An illustrative preferred procedure for preparing the coated granules of medicament is the following:

A solution of the coating polymers is prepared in the organic solvent by simply adding the polymers to the solvent with stirring. The medicament, in granular form, is placed in a fluidized bed coater and is fluidized by a flow of warm air. The temperature of the air has not been found to be narrowly critical, and can vary over a wide range, keeping in mind the fact that the temperature should not be high enough to cause decomposition, sintering, or melting of the medicament granules. When coating APAP granules, a temperature of from about 55° to 75° C. has been found to be suitable. The rate of air flow is adjusted so as to fluidize the granules. Such flow will vary depending on factors such as the specific equipment used, the size of the charge of granules, the size of the individual granules, the apparent specific gravity of the granules, and other factors that are known to the worker in the arts relating to fluidized bed coating. After the medicament has been fluidized, the polymer solution is sprayed on top of the fluidized bed. The air flow through the bed is continued until the amount of solvent remaining in the coating has been reduced to parts per million levels. The granules are actually dry to the touch within a very short time after the coating solution has been sprayed onto the granules of medicament; a matter of a few seconds in some cases. However, the total drying time required to ensure that the solvent content of the coating has been reduced to the level desired may take much longer, depending on the temperature of the air, the size of the batch, and the like. For batches of APAP weighing four to six kilograms, total drying times of the order of one to three hours have been used. Routine experimentation will suffice to determine the appropriate air temperatures and total times required in the fluidized bed coaters in individual cases.

The Examples below set fourth the ingredients and proportions for typical laboratory scale preparations of coated medicament granules. The materials used are the following:

APAP—Acetaminophen USP granules having a particle size of about 60 mesh;

CA—Cellulose acetate NF powder, CA 398-10 from the Food and Pharmaceutical Products Division of FMC. The polymer has an acetyl content of about 39.8%, by weight, a hydroxyl content of 3.4%, by weight, a degree of substitution of 2.7, and a solution viscosity of about 38 poises or 10 seconds, determined by ASTM Method D 1343 in the solution described as Formula A, ASTM Method D 871. (Viscosities in poises are converted to ASTM seconds equivalent to values obtained under ASTM Method D 871.) According to the manufacturer, the typical weight average molecular weight is 177,000 and the typical number average molecular weight is 58,500.

CA 2—Cellulose acetate, CA-320-S from the Food and Pharmaceutical Products Division of FMC. The polymer has an acetyl content of about 32.0%, by weight, a hydroxyl content of about 9.0%, by weight, and a degree of substitution of 2.1. The manufacturer reports a solution viscosity in 90:10 CH$_2$Cl:methanol, at 4% (w/w) concentration, of 50 cps. (The method used to determine the viscosity was not reported.) Typical weight average molecular weight is 100,500 and typical number average molecular weight is 63,500, according to the manufacturer.

PVP—Polyvinyl pyrrolidone (Povidone USP)—Plasdone K29/32 from GAF in powder form. Viscosity of a 5% solution in water at pH 7 and 25° C. is 2.4 centipoises;

CAT—Cellulose triacetate powder, CA-435-75S from FMC. Acetyl content is 43.5 and the solution viscosity is 68 seconds, determined by the "Ball Drop Method" of ASTM D 1343, using the solution designated "Formula D" in Table 2 of ASTM D 871.

Ibuprofen—In the form of granules having a particle size of about 60 mesh;

Loperamide (HCl salt)—In the form of granules having a particle size of about 40–60 mesh;

CAB—Cellulose acetate butyrate, CAB 171-15S from FMC. The polymer has a butyryl content of 17 weight percent, an acetyl content of 29.5 weight percent, and a viscosity of 24 cps in a 4 weight percent solution in methylene chloride:methanol (90:10) one day after solution preparation. The viscosity is taken at about 25° C.;

Tables I through XIV, below, display the identity of the medicament, the coating polymers, the organic solvents in the organic solvent solution of the coating polymers, and the proportions of all of these materials for typical laboratory scale batches of coated medicament granules for use in the invention. The term "total coat" refers to the proportion of coating to medicament in the coated granule product, "charge" to the weight of medicament, "polymer solution" to the proportion of polymer in the organic solvent solution, and "total batch" to the weight of medicament plus coating.

TABLE I

Example 1

| Total Coat | 12% w/w | | |
|---|---|---|---|
| Charge | 4000 gms | APAP | |
| Total Polymer | | | 545.45 gms |
| Polymer 1 | 85% w/w | CA | 463.64 gms |
| Polymer 2 | 15% w/w | PVP | 81.82 gms |
| Polymer Soln | 10% w/w | | 5454.55 gms |
| Solvent 1 | 80% w/w | Acetone | 3927.27 gms |
| Solvent 2 | 20% w/w | Methanol | 981.82 gms |
| | | Total Batch | 4545.45 gms |

TABLE II

Example 2

| Total Coat | 12% w/w | | |
|---|---|---|---|
| Charge | 4000 gms | APAP | |
| Total Polymer | | | 545.45 gms |
| Polymer 1 | 80% w/w | CA | 436.36 gms |
| Polymer 2 | 20% w/w | PVP | 109.09 gms |
| Polymer Soln | 10% w/w | | 5454.55 gms |
| Solvent 1 | 80% w/w | Acetone | 3927.27 gms |
| Solvent 2 | 20% w/w | Methanol | 981.82 gms |
| | | Total Batch | 4545.45 gms |

TABLE III

Example 3

| Total Coat | 12% w/w | | |
|---|---|---|---|
| Charge | 4000 gms | APAP | |
| Total Polymer | | | 545.45 gms |
| Polymer 1 | 85% w/w | CA | 463.64 gms |
| Polymer 2 | 15% w/w | PVP | 81.82 gms |
| Polymer Soln | 8% w/w | | 6818.18 gms |
| Solvent 1 | 90% w/w | Acetone | 5645.45 gms |
| Solvent 2 | 10% w/w | Ethyl acetate | 627.27 gms |
| | | Total Batch | 4545.45 gms |

TABLE IV

Example 4

| Total Coat | 12% w/w | | |
|---|---|---|---|
| Charge | 4000 gms | APAP | |
| Total Polymer | | | 545.45 gms |
| Polymer 1 | 85% w/w | CA 2 | 463.64 gms |
| Polymer 2 | 15% w/w | PVP | 81.82 gms |
| Polymer Soln | 8% w/w | | 6818.18 gms |
| Solvent 1 | 90% w/w | Acetone | 5645.45 gms |
| Solvent 2 | 10% w/w | Ethyl acetate | 627.27 gms |
| | | Total Batch | 4545.45 gms |

TABLE V

Example 5

| Total Coat | 12% w/w | | |
|---|---|---|---|
| Charge | 4000 gms | APAP | |
| Total Polymer | | | 545.45 gms |
| Polymer 1 | 85% w/w | CAT | 463.64 gms |
| Polymer 2 | 15% w/w | PVP | 81.82 gms |
| Polymer Soln | 8% w/w | | 6818.18 gms |
| Solvent 1 | 80% w/w | $CH_2Cl_2$ | 18.18 gms |
| Solvent 2 | 20% w/w | Methanol | 1254.55 gms |
| | | Total Batch | 4545.45 gms |

TABLE VI

Example 6

| Total Coat | 12% w/w | | |
|---|---|---|---|
| Charge | 4000 gms | APAP | |
| Total Polymer | | | 545.45 gms |
| Polymer 1 | 85% w/w | CAT | 463.64 gms |
| Polymer 2 | 15% w/w | PVP | 81.82 gms |
| Polymer Soln | 8% w/w | | 6818.18 gms |
| Solvent 1 | 100% w/w | $CH_2Cl_2$ | 6272.73 gms |
| Solvent 2 | 0% w/w | | 0.00 gm |
| | | Total Batch | 4545.45 gms |

TABLE VII

Example 7

| Total Coat | 15% w/w | | |
|---|---|---|---|
| Charge | 4000 gms | APAP | |
| Total Polymer | | | 705.88 gms |
| Polymer 1 | 85% w/w | CA | 600.00 gms |
| Polymer 2 | 15% w/w | PVP | 105.88 gms |
| Polymer Soln | 10% w/w | | 7058.82 gms |
| Solvent 1 | 80% w/w | $CH_2Cl_2$ | 5082.35 gms |
| Solvent 2 | 20% w/w | Methanol | 1270.59 gms |
| | | Total Batch | 4705.88 gms |

TABLE VIII

Example 8

| Total Coat | 15% w/w | | |
|---|---|---|---|
| Charge | 4000 gms | APAP | |
| Total Polymer | | | 705.88 gms |
| Polymer 1 | 85% w/w | CA | 600.00 gms |
| Polymer 2 | 15% w/w | PVP | 105.88 gms |
| Polymer Soln | 10% w/w | | 7058.82 gms |
| Solvent 1 | 100% w/w | $CH_2Cl_2$ | 6352.94 gms |
| Solvent 2 | 0% w/w | | 0.00 gm |
| | | Total Batch | 4705.88 gms |

TABLE IX

Example 9

| Total Coat | 12% w/w | | |
|---|---|---|---|
| Charge | 4000 gms | APAP | |
| Total Polymer | | | 545.45 gms |
| Polymer 1 | 95% w/w | CA | 518.18 gms |
| Polymer 2 | 5% w/w | PVP | 27.27 gms |
| Polymer Soln | 10% w/w | | 5454.55 gms |
| Solvent 1 | 80% w/w | Acetone | 3927.27 gms |
| Solvent 2 | 20% w/w | Methanol | 981.82 gms |

TABLE IX-continued

Example 9

| | | |
|---|---|---|
| | Total Batch | 4545.45 gms |

TABLE X

Example 10

| | | | | |
|---|---|---|---|---|
| Total Coat Charge | 12% w/w 4000 gms | APAP | | |
| Total Polymer | | | | 545.45 gms |
| Polymer 1 | 90% w/w | CA | | 490.91 gms |
| Polymer 2 | 10% w/w | PVP | | 54.55 gms |
| Polymer Soln | 10% w/w | | | 5454.55 gms |
| Solvent 1 | 80% w/w | Acetone | | 3927.27 gms |
| Solvent 2 | 20% w/w | Methanol | | 981.82 gms |
| | | Total Batch | | 4545.45 gms |

TABLE XI

Example 11

| | | | |
|---|---|---|---|
| Total Coat Charge | 12% w/w 4000 gms | IBUPROFEN | |
| Total Polymer | | | 545.45 gms |
| Polymer 1 | 80% w/w | CA | 436.36 gms |
| Polymer 2 | 20% w/w | PVP | 109.09 gms |
| Polymer Soln | 8% w/w | | 6818.18 gms |
| Solvent 1 | 80% w/w | Acetone | 5018.18 gms |
| Solvent 2 | 20% w/w | Methanol | 1254.55 gms |
| | | Total Batch | 4545.45 gms |

TABLE XII

Example 12

| | | | |
|---|---|---|---|
| Total Coat Charge | 12% w/w 4000 gms | Loperamide HCl | |
| Total Polymer | | | 545.45 gms |
| Polymer 1 | 80% w/w | CA | 436.36 gms |
| Polymer 2 | 20% w/w | PVP | 109.09 gms |
| Polymer Soln | 8% w/w | | 6818.18 gms |
| Solvent 1 | 80% w/w | Acetone | 5018.18 gms |
| Solvent 2 | 20% w/w | Methanol | 1254.55 gms |
| | | Total Batch | 4545.45 gms |

TABLE XIII

Example 13

| | | | |
|---|---|---|---|
| Total Coat Charge | 12% w/w 4000 gms | APAP | |
| Total Polymer | | | 545.45 gms |
| Polymer 1 | 85% w/w | CAB | 463.64 gms |
| Polymer 2 | 15% w/w | PVP | 81.82 gms |
| Polymer Soln | 8% w/w | | 6818.18 gms |
| Solvent 1 | 80% w/w | $CH_2Cl_2$ | 5018.18 gms |
| Solvent 2 | 20% w/w | Methanol | 1254.55 gms |
| | | Total Batch | 4545.45 gms |

TABLE XIV

Example 1

| | | | |
|---|---|---|---|
| Total Coat Charge | 12% w/w 4000 gms | APAP | |
| Total Polymer | | | 545.45 gms |
| Polymer 1 | 85% w/w | CAB | 463.64 gms |
| Polymer 2 | 15% w/w | PVP | 81.82 gms |
| Polymer Soln | 8% w/w | | 6818.18 gms |
| Solvent 1 | 80% w/w | $CH_2Cl_2$ | 5018.18 gms |
| Solvent 2 | 20% w/w | Methanol | 1254.55 gms |
| | | Total Batch | 4545.45 gms |

While the use of fluidized bed coating has been described in some detail as one preferred method for making the coated granules that are utilized in the invention, other techniques for making the coated granules may be used. Such other techniques include various microencapsulation techniques such as coacervation and solvent evaporation.

PREPARATION OF CHEWABLE TABLETS

Example 15

The ingredients displayed in Table XV, below, were sieved, dry blended, and compressed by standard procedures into a round (disc shaped) chewable tablets, each weighing 1100 milligrams. The tablets had diameters of 9/16 inch, thicknesses of 0.573 centimeter, and had volumes of 0.919 cubic centimeter. Each tablet contained 325 milligrams of active ingredient (APAP). The table displays the ingredients, the weight, in milligrams, of each ingredient in each tablet, and the weight, in grams, of each ingredient in the batch mix, which was sufficient to make 350 tablets. The coated APAP granules used were similar to those described above in Example 1 which contain 12 weight percent coating in which the CA:PVP proportion is 85:15% w/w.

TABLE XV

| Component | Mg/Tablet | Percent | Gms/Batch |
|---|---|---|---|
| Mannitol | 622.91 | 56.63 | 218.017 |
| Avicel PH101 | 73.07 | 6.64 | 25.574 |
| Aspartame | 12.06 | 1.10 | 4.220 |
| Citric acid (anhy) | 5.85 | 0.53 | 2.046 |
| Fruit punch | 4.38 | 0.40 | 1.534 |
| Prosweet | 2.92 | 0.27 | 1.023 |
| Mg Stearate | 9.50 | 0.86 | 3.325 |
| Coated APAP | 369.32 | 33.57 | 129.261 |

Example 16

By the procedure described in Example 15, chewable tablets were prepared having 325 mg of active APAP per tablet, from coated granules containing 15 weight percent coating in which the proportion of CA:PVP was 85:15% w/w, similar to those described above in Example 7. The table below displays the ingredients, Mg/tablet, percent, and grams/batch sufficient to make 10,000 tablets.

TABLE XVI

| Component | Mg/Tablet | Percent | Gms/Batch |
|---|---|---|---|
| Mannitol | 611.79 | 55.62 | 6117.94 |
| Avicel PH101 | 71.76 | 6.52 | 717.65 |
| Aspartame | 11.84 | 1.08 | 118.41 |
| Citric acid (anhyd) | 5.74 | 0.52 | 57.41 |
| Fruit punch | 4.31 | 0.39 | 43.06 |
| Prosweet | 2.87 | 0.26 | 28.71 |
| Mg Stearate | 9.33 | 0.85 | 93.29 |
| Coated APAP | 382.85 | 34.76 | 3823.53 |

The following table displays typical proportion ranges for the ingredients that were used in Examples 15 and 16:

TABLE XVII

| Component | Range of Proportions, % |
|---|---|
| Mannitol | 30–70 |
| Avicel PH101 | 5–12 |
| Aspartame | 0.5–3 |
| Citric acid | 0.1–2 |
| Fruit punch | 0.2–2 |
| Prosweet | 0.1–2 |
| Mg Stearate | 0.4–2 |
| Coated APAP | 10–50 |

The functions of the several ingredients and some typical replacements for them are as follows:

Mannitol is a sweetener. It can be replaced by dextrose, fructose, sorbitol, compressible sugar, or lactose;

Avicel PH101 is microcrystalline cellulose. It is used as a binder, and can be replaced with other binders such as alginic acid, carboxymethyl cellulose, hydroxypropyl methyl cellulose, PVP, or starch;

Aspartame is an artificial sweetener. It can be replaced with others such as sacchirin;

Citric acid is used as an acidifying agent to enhance the taste. It can be replaced by other acidifying agents such as phosphoric acid;

The fruit punch flavoring agent can be replaced with other flavoring agents, such as vanilla, peppermint, orange, cherry, or spearmint;

Prosweet is another sweetener. It can be replaced with other materials such as saccharin, aspartame, natural sugars; and Magnesium stearate is a lubricant (to lubricate the dye walls and punches used during the tablet compression procedure). It can be replaced by talc, stearic acid, calcium stearate, zinc stearate, or the like.

Example 17 and Control Example 1

In this experiment, chewable tablets were made by procedures analogous to that described above in Example 15 from coated APAP granules having a CA/PVP coating in accordance with this invention (coated granule size was 40–60 mesh). A second batch of chewable tablets were made by an analogous procedure from coated APAP granules having a coating of ethyl cellulose (coated granule size was 40–60 mesh). The two batches of tablets were tested in a blind taste panel test by thirty persons. Tables XVIII and XIX, below, display the formulations used in each batch of tablets. The tablets made in accordance with this invention were made from coated granules containing 14.4 weight percent coating wherein the proportion of CA to PVP was 85:15% w/w. The tablets made in accordance with the prior art were made from coated granules containing 9.4 weight percent ethyl cellulose coating. The two batches of tablets had approximately equal bioavailability of the active medicament, as evidenced by dissolution tests (the procedures of which are described below in Example 18), even though the tablets of the invention were made from coated granules having a larger proportion of coating.

TABLE XVIII

| Component | Example 17 | | |
|---|---|---|---|
| | Mg/Tablet | Percent | Gms/Batch |
| Mannitol | 614.08 | 55.83 | 214.93 |
| Avicel PH101 | 72.03 | 6.55 | 24.21 |
| Aspartame | 11.89 | 1.08 | 4.16 |
| Citric Acid | 5.76 | 0.52 | 2.02 |
| Fruit Punch | 4.32 | 0.39 | 1.51 |
| Prosweet | 2.88 | 0.26 | 1.01 |
| Mg Stearate | 9.36 | 0.85 | 3.28 |
| CA/PVP Coated APAP | 379.67 | 34.52 | 132.89 |

TABLE XIX

| Component | Control Example 1 | | |
|---|---|---|---|
| | Mg/Tablet | Percent | Gms/Batch |
| Mannitol | 631.94 | 57.45 | 221.18 |
| Avicel PH101 | 74.13 | 6.74 | 25.95 |
| Aspartame | 12.73 | 1.11 | 4.28 |
| Citric Acid | 5.93 | 0.54 | 2.08 |
| Fruit Punch | 4.45 | 0.40 | 1.56 |
| Prosweet | 2.97 | 0.27 | 1.04 |
| Mg Stearate | 9.64 | 0.88 | 3.37 |

TABLE XIX-continued

| Component | Control Example 1 | | |
|---|---|---|---|
| | Mg/Tablet | Percent | Gms/Batch |
| Et Cell Coated APAP | 358.72 | 32.61 | 125.55 |

The blind taste test was carried out as follows:

Each participant was given two tablets, one being a tablet of Example 17 and the other being a tablet of Control Example 1. The two tablets were labelled in such a way that the participant did not know their identity. The participant was instructed to chew one tablet first (half the participants were instructed to chew the tablet of Example 17 first, and half the Control tablet first), then eat one or two Premium low salt crackers, and then chew the other tablet. Each was requested to state which tablet tasted better to him or her (participants were required to select one or the other), and to state whether or not the participant thought that each was acceptable as an adult dosage chewable tablet. Seventy percent (70%) of the participants preferred the taste of the tablet of Example 17 over the Control tablet (this is a statistically significant difference); 25 of the 30 thought that the Control tablet was acceptable and 26 thought that the Example 17 tablet was acceptable (this difference is not statistically significant).

Example 18

In order to demonstrate the variation in bioavailability (as evidenced by dissolution rates) that can be obtained by varying the CA to PVP ratio in the coating on the coated granules of medicament, and by varying the proportion of coating to medicament in the coated granules, a series of tablets containing 325 mg of active APAP were made by procedures analogous to those described above. The formulations used in the tablets were similar to those described in Tables XV, XVI, and XVII, with the proportions of the inert ingredients remaining the same (with respect to each other), and the proportion of coated granules being varied so as to yield tablets having 325 mg of APAP. One tablet at a time was gently crushed in a mortar and pestle to produce uniform granules about 1–2 mm in size. The crushed tablet was then immersed in dissolution baths, each of which contained 900 milliliters of USP simulated gastric juice without enzymes, which was stirred at 37° C. by a USP dissolution paddle rotating at 100 rpm. Aliquots were taken from each dissolution bath at intervals of 5, 10, 20, 30, and 40 minutes, and the removed samples were analyzed for APAP content by HPLC. The results were plotted on the graphs that are presented as FIGS. 1 and 2. The graph shown as FIG. 1 plots percent dissolution of APAP versus time in minutes for a series of four different formulations wherein the proportion of PVP in the coating was 0%, 15%, 20%, or 25%. The proportion of coating in these coated granules varied from about 17.2 to 17.7 weight percent, with a mean of about 17.4 weight percent. The graph shown as FIG. 2 plots percent dissolution of APAP versus time in minutes for tablets wherein the proportion of coating to APAP in the granules was 12.3%, 13.8%, and 14.4%. In each case, the CA to PVP proportion in the coating was 85:15 CA:PVP w/w %. As can be seen from the graphs, the dissolution rate is inversely proportional to the proportion of coating to medicament in the coated granules, and directly proportional to the proportion of PVP in the coating. Studies similar to these can be utilized to determine the desired CA/PVP ratios and coating proportions to be used in individual cases in order to obtain rapid release or sustained release of the medicament.

What is claimed is:

1. A chewable tablet of a medicament comprising compressed coating granules, said coated granules individually comprising medicament coated with a blend of (a) cellulose acetate or cellulose acetate butyrate and (b) polyvinyl pyrrolidone.

2. The chewable tablet of claim 1 wherein the medicament is acetyl p-aminophenol.

3. The chewable tablet of claim 1 wherein the blend contains from about 80 to about 97 weight percent of cellulose acetate, the remainder being polyvinyl pyrrolidone.

4. The chewable tablet of claim 2 wherein the blend contains from about 80 to about 97 weight percent of cellulose acetate, the remainder being polyvinyl pyrrolidone.

5. The chewable tablet of claim 1 wherein the coated granules contain from about 5 to about 20 weight percent of said blend.

6. The chewable tablet of claim 2 wherein the coated granules contain from about 5 to about 20 weight percent of said blend.

7. The chewable tablet of claim 3 wherein the coated granules contain from about 5 to about 20 weight percent of said blend.

8. The chewable tablet of claim 4 wherein the coated granules contain from about 5 to about 20 weight percent of said blend.

* * * * *

UNITED STATES PATENT AND TRADEMARK OFFICE
CERTIFICATE OF CORRECTION

PATENT NO. : 4,851,226

DATED : July 25, 1989

INVENTOR(S) : Julian et al.

It is certified that error appears in the above-identified patent and that said Letters Patent is hereby corrected as shown below:

Col. 13, claim 1, line 2: "coating" should read --coated--.

Signed and Sealed this

Eighteenth Day of June, 1991

*Attest:*

HARRY F. MANBECK, JR.

*Attesting Officer*      *Commissioner of Patents and Trademarks*